United States Patent [19]

Task

[11] Patent Number: 4,615,594
[45] Date of Patent: Oct. 7, 1986

[54] VISION TEST CHART AND METHOD USING GAUSSIANS

[75] Inventor: Harry L. Task, Dayton, Ohio

[73] Assignee: The United States of America as represented by the Secretary of the Air Force, Washington, D.C.

[21] Appl. No.: 693,927

[22] Filed: Jan. 23, 1985

[51] Int. Cl.$^4$ .............................................. A61B 3/02
[52] U.S. Cl. ..................................... 351/239; 351/243
[58] Field of Search ............... 351/239, 240, 241, 242, 351/243, 246

[56] References Cited

U.S. PATENT DOCUMENTS

| | | |
|---|---|---|
| 2,385,992 | 10/1945 | Jobe . |
| 2,463,813 | 3/1949 | Shepard . |
| 3,490,832 | 1/1970 | Mitsuishi et al. . |
| 4,155,632 | 5/1979 | Wolbarsht . |
| 4,212,520 | 7/1980 | Klimsa . |
| 4,293,200 | 10/1981 | Dobson et al. . |
| 4,324,459 | 4/1982 | Gerharz . |
| 4,365,873 | 12/1982 | Ginsburg . |

OTHER PUBLICATIONS

"Spatial Sine-Wave Responses of the Human Visual System", by A. Watanabe et al., Vision Res, 8, 1245–1263 (1968).
"Effect of Focus on the Visual Response to a Sinusoidally Modulated Spatial Stimulus", by D. G. Green et al., J Opt Soc Am, 55:9, 1154–1157 (1965).
"Optical and Retinal Factors Affecting Visual Resolution", by F. W. Campbell et al., J Physiol, 81, 576–593 (1965).
"Some Remarks on Ophthalmic Test Types", by L. Ronchi et al. (1972).
"A New Contrast Sensitivity Vision Test Chart", by A. P. Ginsburg, Am J Optometry & Physiological Optics, 61:6, 403–407 (1984).
"Proposed New Vision Standards for the 1980's and Beyond: Contrast Sensitivity", by A. P. Ginsburg, AFAMRL-TR-80-121 (1981).
"Modulations Thresholds for Sinusoidal Light Distributions on the Retina", by G. Westheimer, J. Physiol 152, 67–74 (1960).
"Stimulus Patterns for Visual Research", by D. H. Kelly, J Opt Soc Am, 50:1, 1115–1116 (1960).
"Visual Responses to Time–Dependent Stimuli. I. Amplitude Sensitivity Measurements", by D. H. Kelly, J Opt Soc Am, 51:4, 422–429 (1961).

Primary Examiner—Rodney B. Bovernick
Attorney, Agent, or Firm—Bobby D. Scearce; Donald J. Singer

[57] ABSTRACT

A novel vision test device and method for measuring the ability of a subject to perceive contrasts is described, which comprises a chart for display to the subject having a plurality of visual test shapes systematically organized thereover in a predetermined array on a background of preselected luminance or reflectance level, each test shape having a preselected luminance level providing maximum contrast relative to background at its center and substantially zero contrast relative to background at its edges, the luminance (or reflectance) level of each test shape varying radially from its center outwardly according to a Gaussian distribution of preselected distribution factor.

10 Claims, 5 Drawing Figures

VISION TEST CHART AND METHOD USING GAUSSIANS

RIGHTS OF THE GOVERNMENT

The invention described herein may be manufactured and used by or for the Government of the United States for all governmental purposes without the payment of any royalty.

BACKGROUND OF THE INVENTION

The present invention relates generally to human vision testing devices and methods, and more particularly to a novel vision test chart and method for testing the ability of a subject to perceive contrast, and more specifically to perceive contrast as a function of size.

Numerous visual test pattern configurations and methods for testing the ability of a subject to visually distinguish shapes, sizes and contrasts have been proposed. Typically, these patterns have been characterized by variations of size and contrast of shapes having substantially well defined edges, such as Snellen charts, tumbling "E" arrays, Landolt "C" charts, etc. Certain of the prior art patterns are aperiodic, such as disks, rectangles, diamonds, etc.; others are quasi-periodic, such as tri-bar and tumbling "E" arrays, and small checkerboard designs; still others are periodic, such as square waves and sine waves. Only the pattern comprising a sine wave has been characterized by spatially varying luminance as an exception to the stated groups of shapes otherwise characterized by clearly defined edges. Sine wave patterns do not have spatial characteristics like visual objects in the real world, but do have "fuzzy edges", somewhat similar to real objects of varying luminance without sharply defined edges. An advantage of aperiodic patterns is that they require only a small area for the shape comprising the pattern, and may thereby be made substantially similar to real objects. In the prior art, therefore, the expedient has been to test a "single" spatial frequency; in so doing, relatively large size patterns of about three degrees of arc and larger have generally been utilized.

The present invention substantially eliminates the aforementioned problems in the prior art by providing a superior vision test chart and method for rapidly and reliably testing a subject for ability to perceive contrast, and more specifically to perceive contrast as a function of size. The chart and method of the invention include the advantages of both periodic and aperiodic targets without the attendant disadvantages. The novel visual test chart of the invention comprises an array of visually contrasting test shapes or spots of various sizes and contrasts on a contrasting background, each shape being characterized by a Gaussian luminance (or reflectance) distribution across the width of the shape. Each visual test shape of the chart has a reasonably bounded spatial frequency spectrum (i.e., no sharp edges). The array of the chart may preferably comprise rows and columns, wherein the shapes systematically vary in size within each row and in maximum contrast within each column. The method taught herein provides rapid and comprehensive visual contrast perception measurement and allows rapid mathematical analysis of the test results, since Gaussian distributions may be conveniently manipulated analytically.

It is, therefore, a principal object of the present invention to provide an improved method for rapidly testing the ability of a subject to perceive contrasts.

It is a further object of the invention to provide an improved contrast vision test chart.

These and other objects of the invention will become apparent as the detailed description of certain representative embodiments thereof proceeds.

SUMMARY OF THE INVENTION

In accordance with the foregoing principles and objects of the present invention, a novel vision test device and method for measuring the ability of a subject to perceive contrasts is described, which comprises a chart for display to the subject having a plurality of visual test shapes systematically organized thereover in a predetermined array on a background of preselected luminance or reflectance level, each test shape having a preselected luminance level providing maximum contrast relative to background at its center and substantially zero contrast relative to background at its edges, the luminance (or reflectance) level of each test shape varying radially from its center outwardly according to a Gaussian distribution of preselected distribution factor.

DESCRIPTION OF THE DRAWINGS

The present invention will be more clearly understood from the following detailed description of representative embodiments thereof read in conjunction with the accompanying drawings wherein.

DETAILED DESCRIPTION

Figure 1:
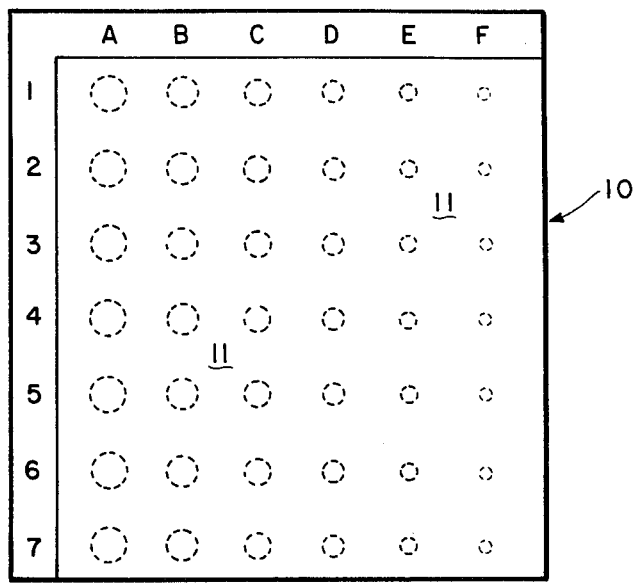
FIG. 1 is a representative vision test chart comprising an array of test shapes each having a Gaussian luminance distribution according to the present invention.

Referring now to FIG. 1, shown therein is a representative test chart 10 of the present invention including an array of test shapes for viewing by a subject in testing the ability of the subject to perceive contrasts. Chart 10 may be of any convenient size or may comprise any convenient display medium suitable for presentation to a subject of the test shapes in the method of the present invention. For example, chart 10 may comprise a wall chart, flash card, transparency or other projectable image, or the like, for viewing by a subject situated a predetermined distance from the chart.

Chart 10 may comprise a plurality of rows and columns (numbered and lettered, respectively, for identification purposes) of test shapes $A_1, A_2, \ldots B_1, B_2, \ldots$, in predetermined array on contrasting background, such as the rectangular array displayed in FIG. 1. The array may comprise any number of rows and columns of test shapes, and other arrays may be formulated, such as circular, spiral, etc., as might occur to one with skill in the field of the invention. Each test shape comprises a small solid spot of preselected size and shape characterized by a Gaussian luminance (or reflectance) distribution from the center radially outwardly. The discussion hereinafter presented describes the contrast distribution across each test shape in terms of radially varying luminous levels on a contrasting background, and it is understood that within the scope of the teachings of the present invention, such terminology shall apply to both positive and negative contrasts of the test shapes relative to background. The shapes as shown in FIG. 1 are circular, but other shapes, such as ovals, may be utilized, although for such alternative shapes, the corresponding Gaussian contrast distribution would be somewhat more complicated than that for circular shapes. In the non-limiting array suggested in FIG. 1, test shapes $X_i$ (where X refers generally to a lettered column, and i refers to a numbered row) display increasing contast (relative to background 11) down a column, and decreasing size across a row.

The fundamental equation which describes the Gaussian radial luminance distribution of a given test shape $X_i$ may generally be presented mathematically as:

$$G = L_b - L_T \exp\left[\frac{-x^2}{2\sigma^2}\right] \quad (1)$$

where $(L_b - L_T)$ is the maximum contrasting luminance level of the particular test shape, $L_b$ is the luminance level of the background, $\sigma$ (sigma) is the standard deviation or distribution factor of the Gaussian distribution, and x is the radial parameter for the test shape. Note that $L_T$ itself may not be a real physical luminance and may take on negative values. An alternative form of the Gaussian Equation (1) may be given by:

$$G_o = L_o\left(1 - k\exp\left[\frac{-x^2}{2\sigma^2}\right]\right) \quad (2)$$

where the maximum contrasting luminance level for a test shape $X_i$ is represented as a fraction $(1-k)$ of the background level $L_o$, and $0 \leq k \leq 1$. The alternate Equation (2) may be more convenient for describing the characteristics of test shapes $X_i$, although it is understood that characteristic maximum contrasting luminance levels of the test shapes in an array shall not be limited to a function of the background level within the scope of the teachings of this invention. Further, the contrast C (where contrast is defined as the maximum luminance minus the minimum luminance divided by the sum of the two) for each test shape may be represented by:

$$C = \frac{L_T}{2L_b - L_T} \quad (3)$$

where the terms on the right side of Equation (3) correspond to those on the right side of Equation (1). For the alternative form corresponding to Equation (2), the contrast $C_o$ for a test shape may be expressed as:

$$C_o = \frac{k}{2 - k} \quad (4)$$

In accordance with the teachings of the present invention, the critical features of each contrasting test shape are the contrast as defined by Equation (3) or (4) above, and the "size" of the test shape, which is governed by the value of sigma appearing in the Gaussian luminance distribution expression (Equations (1) or (2)). Size and contrast distribution for each test shape $X_i$ may be varied by changing $\sigma$ and/or $L_T$.

Figure 2:
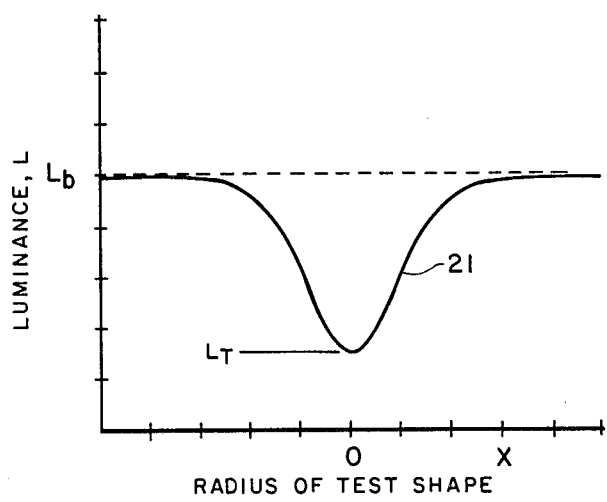
FIG. 2 is a graph a of Gaussian luminance distribution for a representative test shape of the test chart of FIG. 1.
Figure 3:
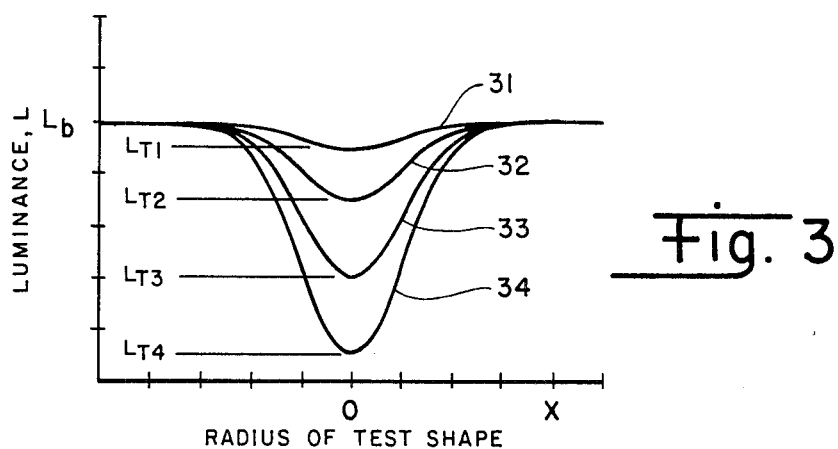
FIG. 3 presents graphs of four Gaussian luminance distributions for test shapes of the present invention, having equal distribution factor and various maximum contrasting luminance levels.

The contrast distribution for each contrasting test shape $X_i$ of FIG. 1 (as compared to the luminance level $L_b$ of background 11 surrounding each test shape) may be as represented by the general plot of luminance L versus test shape radius x as suggested in FIG. 2. Referring now to FIG. 2, each test shape $X_i$ has a radially outwardly varying contrast luminance distribution governed by a Gaussian distribution 21 of characteristic sigma and maximum contrasting luminous level $(L_b - L_T)$ according to Equation (1) or (2) above, on a background characterized by a contrasting luminous level $L_b$. FIG. 3 illustrates a series of Gaussian distributions 31,32,33,34 for four corresponding test shapes characterized by the same sigma and having different maximum contrasting luminous parameter levels $L_{T1}, L_{T2}, L_{T3}, L_{T4}$, respectively, on contrasting background $L_b$, while FIG. 4 illustrates a series of Gaussian distributions 41,42,43 for three corresponding test shapes characterized by different sigmas and having the same maximum contrasting luminous parameter level $L_T$ on contrasting background $L_b$.

Figure 4:
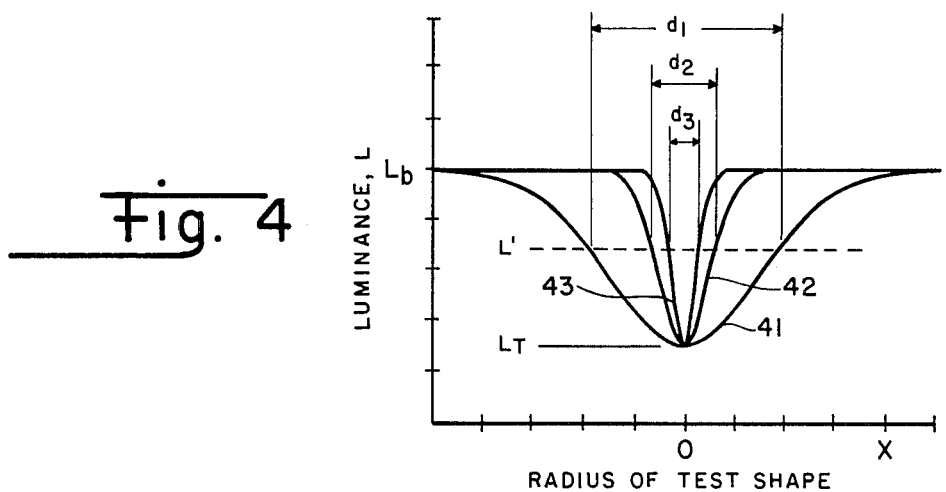
FIG. 4 presents graphs of Gaussian distributions for three test shapes having the same maximum contrasting luminance level and various distribution factors.

As suggested in FIGS. 3 and 4, each test shape may be characterized by a size which is not well defined, since each test shape fades in contrast at its radial extremes into the background according to the corresponding Gaussian distribution. However, according to the principles governing the present invention, a "radius" for each Gaussian distribution (characteristic of a specific test shape $X_i$) may be defined (for the purposes of organizing a test chart and of collecting, correlating and evaluating data on a subject) in terms of the corresponding characteristic sigma. As illustrated in FIG. 4, the width $d_i$ of each Gaussian distribution may be determined at one-half the maximum contrasting luminous level L'. This gives a value for the radius $r_i$ of each test shape as 1.1774 times the corresponding sigma, which is close enough to the value of sigma that, alternatively, "radius" of each test shape may be simply defined as equal to sigma, i.e., $r_i = \sigma_i$.

In order to devise and organize a test chart 10 (FIG. 1) containing a plurality of test shapes $X_i$ each of characteristic "size" and total contrasting luminance $L_T$, one may generate a first plurality of test shapes characterized by the same $L_T$ and by different values of sigma, and a second plurality characterized by the same sigma and different values of $L_T$. Accordingly, test chart 10 of FIG. 1 may comprise as a column X a series of test shapes including those characterized by $L_{T1}, L_{T2}, L_{T3}, L_{T4}$, and equal corresponding sigma (i.e., equal radii), as presented in FIG. 3. Similarly, a row i of chart 10 may comprise test shapes including those characterized by equal $L_T$ and different sigmas defining corresponding diameters $d_1, d_2, d_3$ such as presented in FIG. 4. Therefore all $A_i$ may have the same radius, all $B_i$ may have the same radius (smaller than $A_i$), etc, and the maximum contrast of each element in a row i may be held constant with each successive row having higher contrast, but such arrangements are not exhaustive of those contemplated herein and therefore are not limiting of the invention. A large family of arrays of test shapes $X_i$, each having a Gaussian luminance distribution, such as the representative array shown in FIG. 1, may thus be generated.

It is instructive to note that the Fourier transform of a Gaussian distribution is itself a Gaussian distribution, however, the Fourier transform represents the spatial frequency spectrum of the corresponding Gaussian test shape defined herein. Therefore, the Gaussian test shapes of the present invention are quasi-bounded in spatial frequency content.

Figure 5:
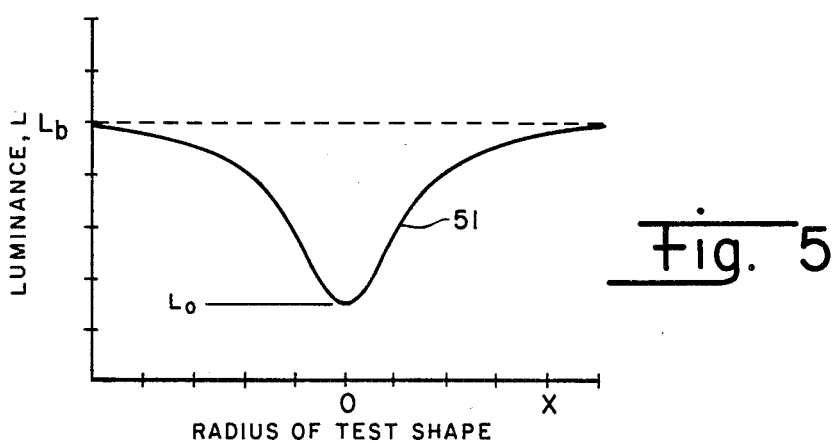
FIG. 5 is a graph of a compound Gaussian distribution characteristic of one embodiment of test shapes of the present invention.

Consider now a contrast test shape characterized by a compound Gaussian distribution, such as that represented by distribution 51 of FIG. 5, which may be desirable in certain applications of the invention herein. In certain situations, it may not be practical to produce a test shape characterized by a simple Gaussian distribution, but it may be practical to produce a shape very closely characterized by a compound Gaussian. A compound Gaussian test shape may, for the purposes of this discussion be defined as a test shape characterized by the superposition of two or more Gaussian distributions of different $L_T$ and/or sigma, either concentrically superimposed or having different centers. A representative Gaussian equation defining the concentric superposition of two simple Gaussians having respective $k_1, k_2$ and $\sigma_1, \sigma_2$ may be represented by:

$$G_{1,2} = L_o\left(1 - k_1\exp\left[\frac{-x^2}{2\sigma_1^2}\right] - k_2\exp\left[\frac{-x^2}{2\sigma_2^2}\right]\right) \quad (5)$$

and the superposition of two non-concentric Gaussians may be given by:

$$G'_{1,2} = L_o\left(1 - k\exp\left[\frac{-(x - x_o)^2}{2\sigma^2}\right] - k\exp\left[\frac{-(x + x_o)^2}{2\sigma^2}\right]\right) \quad (6)$$

FIG. 5 presents a representative plot 51 of a composite Gaussian distribution such as defined by Equation (5). It is noteworthy that a family of test shapes characterized by compound Gaussians such as represented by either Equation (5) or (6) may be generated in manner similar to that whereby shapes having simple Gaussian distributions may be generated as defined above. However, the fundamental shape of the distribution is different from that of a simple Gaussian, and the "size" or "radius" can no longer be specified as a simple term or expression (i.e., such as sigma).

In the method of the present invention for testing the ability of a subject to perceive contrasts as functions of size, a vision chart such as the representative chart 10 of FIG. 1 is displayed to the subject at a preselected viewing distance. The subject is then asked to indicate which test shapes from the array $X_i$ he can see, beginning with the largest and highest contrast shapes (such as $A_7$), and progressing to the smallest and least contrasting shapes which the subject can identify at the preselected distance from the chart. The viewing distance is then changed and the procedure repeated, and information generated from the tests charted, from which results the subject's ability to perceive contrast as function of size may be identified and compared to an average or norm for the classification of individuals to which the subject belongs.

The present invention, as herein described, therefore comprises an improved test chart and measurement method for testing the ability of a subject to perceive contrasts. It is understood that certain modifications to the invention as described may be made, as might occur to one skilled in the field of this invention, within the scope of the appended claims. Therefore, all embodiments contemplated hereunder which achieve the objects of the present invention have not been shown in complete detail. Other embodiments may be developed without departing from the spirit of the invention or from the scope of the appended claims.

I claim:

1. A vision test device for measuring the ability of a subject to perceive contrasts, comprising:
    a. a chart for viewing by said subject, said chart having a plurality of visual test shapes systematically organized thereover in a predetermined array on a background having a preselected background luminance level; and
    b. each said test shape having a preselected contrast luminance level providing a maximum contrast relative to said background at the center thereof, and providing substantially zero contrast relative to said background at the edges thereof, the luminance level of each said test shape varying radially from its center outwardly to its edges according to a Gaussian distribution of preselected characteristic distribution factor.

2. The vision test device as recited in claim 1 wherein said test shapes are circular and are arranged in a rectangular array of rows and columns.

3. The vision test device as recited in claim 2 wherein the test shapes in each row have a characteristic preselected contrast luminance level and vary systematically in preselected distribution factor.

4. The vision test device as recited in claim 1 wherein the contrast luminance level of said test shapes vary radially according to a compound Gaussian distribution.

5. The vision test device as recited in claim 2 wherein the test shapes in each row have a characteristic preselected contrast luminance level and each column has a characteristic preselected distribution factor.

6. A method for measuring the ability of a subject to perceive contrasts, which comprises the steps of:
    a. providing a chart for viewing by said subject, said chart having a plurality of visual test shapes systematically organized thereover in a predetermined array on a background having a preselected background luminance level, each said test shape having a preselected contrast luminance level providing a maximum contrast relative to said background at the center thereof, and providing substantially zero contrast relative to said background at the edges thereof, the luminance level of each said test shape varying radially from its center outwardly to its edges according to a Gaussian distribution of preselected characteristic distribution factor;
    b. displaying said chart in the view of said subject at successively shorter distances to determine the greatest distance at which said subject can distinguish each said test shape from the said background; and
    c. recording said distance for each said test shape.

7. The method as recited in claim 6 wherein said test shapes are circular and are arranged in a rectangular array of rows and columns.

8. The method as recited in claim 7 wherein the test shapes in each row have a characteristic preselected contrast luminance level and vary systematically in preselected distribution factor.

9. The method as recited in claim 6 wherein the contrast luminance level of said test shapes vary radially according to a compound Gaussian distribution.

10. The method as recited in claim 7 wherein the test shapes in each row have a characteristic preselected contrast luminance level and each column has a characteristic preselected distribution factor.

* * * * *